United States Patent

Zhong

(10) Patent No.: US 11,820,741 B2
(45) Date of Patent: Nov. 21, 2023

(54) SEBACIC ACID BY-PRODUCT FATTY ACID POLYESTER POLYOL FOR POLYURETHANE CONTROLLED-RELEASE FERTILIZER ENVELOPE, PREPARATION METHOD THEREOF AND ENVELOPE

(71) Applicant: Maoshi Agricultural Technology Co., Ltd, Anhui (CN)

(72) Inventor: Chenghu Zhong, Anhui (CN)

(73) Assignee: Maoshi Agricultural Technology Co., Ltd, Anhui (CN)

( * ) Notice: Subject to any disclaimer, the term of this patent is extended or adjusted under 35 U.S.C. 154(b) by 0 days.

(21) Appl. No.: 17/589,525

(22) Filed: Jan. 31, 2022

(65) Prior Publication Data

US 2022/0153678 A1 May 19, 2022

(30) Foreign Application Priority Data

Jun. 2, 2021 (CN) .......................... 202110614323.X

(51) Int. Cl.
  *C07C 67/03* (2006.01)
  *C07C 51/493* (2006.01)
  *C08G 18/36* (2006.01)
  *C08G 18/42* (2006.01)
  *C08G 63/78* (2006.01)

(52) U.S. Cl.
  CPC .......... *C07C 67/03* (2013.01); *C07C 51/493* (2013.01); *C08G 18/36* (2013.01); *C08G 18/42* (2013.01); *C08G 63/78* (2013.01)

(58) Field of Classification Search
  CPC .......... A23L 17/00; A23L 17/30; A23L 33/40; A23L 5/20; A23V 2002/00; A23V 2200/304; A61K 38/00; A61K 39/00; A61K 39/35; A61K 39/0005; A61P 37/08; C07C 51/493; C07C 67/03; C07K 14/435; C07K 14/461; C07K 14/47; C08G 18/36; C08G 18/42; C08G 18/4288; C08G 18/7664; C08G 2310/00; C08G 63/48; C08G 63/676; C08G 63/78; C12N 15/09; C12Q 1/48; C12Q 1/6883; C12Q 1/6888; G01N 2800/24; G01N 33/53; G01N 33/564; G01N 33/68; G01N 33/6854; G01N 33/6893; C05G 5/37; C09D 175/06
  See application file for complete search history.

(56) References Cited

U.S. PATENT DOCUMENTS 2,317,668 A * 4/1943 Cheetham .............. C08G 63/12
                                                              528/304

* cited by examiner

*Primary Examiner* — Jafar F Parsa
*Assistant Examiner* — Blaine G Doletski

(57) ABSTRACT

A polyester polyol is synthesized through an esterification reaction with a sebacic acid by-product fatty acid as a raw material; wherein the sebacic acid by-product fatty acid is refined from a by-product produced during preparing a sebacic acid from a castor oil; the sebacic acid by-product fatty acid includes, in weight percentage: a palmitic acid 15-25%, a stearic acid 10-16%, an oleic acid 45-57%, and a linoleic acid 12-28%. A method for preparing the polyester polyol is provided, as well as a polyurethane controlled-release fertilizer envelope and a polyurethane controlled-release fertilizer. The sebacic acid by-product fatty acid is used as a raw material to synthesize the polyester polyol because of a low price. The prepared fertilizer has excellent envelope and controlled-release performance, product structure performance is stable, cost performance is high, and degradation performance is sufficient after being applied to soil.

2 Claims, No Drawings

SEBACIC ACID BY-PRODUCT FATTY ACID POLYESTER POLYOL FOR POLYURETHANE CONTROLLED-RELEASE FERTILIZER ENVELOPE, PREPARATION METHOD THEREOF AND ENVELOPE

CROSS REFERENCE OF RELATED APPLICATION

The present invention claims priority under 35 U.S.C. 119(a-d) to CN 202110614323.X, filed Jun. 2, 2021.

BACKGROUND OF THE PRESENT INVENTION

Field of Invention

The present invention relates to a technical field of envelope materials for controlled-release fertilizers, and more particularly to a sebacic acid by-product fatty acid polyester polyol for a polyurethane controlled-release fertilizer envelope, a preparation method thereof and an envelope.

Description of Related Arts

Sebacic acid is a main raw material for nylon fibers. Chinese sebacic acid production accounts for about 90% of the world's total. Conventionally, Chinese preparation method uses castor oil as a raw material. Castor oil is prepared through hydrolysis, cracking, acidification and other steps, wherein a large number of by-products are produced. These by-products mainly contain fatty acids and their sodium soaps, as well as water, phenol and organic polymer components. Fatty acid is the main by-product in the production process of sebacic acid (referred to as decanoate), accounting for 60% of the production of sebacic acid. The by-product fatty acid is processed with high temperature cracking, the composition and properties thereof are fundamentally different from those of the original oil, including the addition of phenolic substances which are very harmful to the environment and the human body. Due to complex composition and difficult separation, such by-product is usually discarded. On the one hand, it causes environmental pollution. On the other hand, the valuable fatty acids contained in the by-product are not fully utilized, which is a great waste. The added value of fatty acids is very low, the price is also low. Furthermore, there is few market demands, leading to large backlog, which will cause a great burden on the production of the sebacic acid.

Conventionally, sebacic acid by-product fatty acid is mainly used to: synthesize lubricating grease, lubricants and surfactants; prepare biodiesel and soap; and even be discarded since the industrial value is low. However, there is almost no report on the synthesis of polyester polyol polyurethane controlled-release envelope material with the sebacic acid by-product fatty acid.

Chinese patent application CN 201210137099.0 disclosed a method for preparing polyester polyol from waste oil, which comprises steps of: mixing and reacting the waste oil, a catalyst and an initiator for 1-5 hours, and using a nitrogen or inert gas for protecting during reaction; heating to 100-300° C.; mixing a reaction product obtained by the above steps with phthalic anhydride for 5-10 hours, and using the nitrogen or inert gas for protecting during reaction, and heating to 100-300° C.; mixing a reaction product obtained by the above steps with sodium carbonate, and reacting for 1-3 hours; vacuuming and dehydrating during reaction, and heating to 100-150° C., until a vacuum degree is less than 0.08 MPa. Although this application can use waste oil to prepare polyester polyol, the method cannot be widely used due to the complicated and unstable composition of the waste oil, high production cost and complicated processes.

Chinese patent application CN 201310655152.0 disclosed a method for preparing a waste oil modified polyester polyol by using recycled alcohol and waste oil, which comprises steps of: putting low molecular polyol raw materials, waste oil and a catalyst into a polyester reactor, heating to 140-150° C., and reacting for 1-1.5 h; injecting N2, heating to 180-190° C., and reacting for 1.5-2 h; heating to 220-230° C. and keeping for 4-5 h; and then cooling to 120° C., stopping the nitrogen, vacuuming, and reacting for 1.5-2 h until a product moisture is ≤0.07; finally, cooling to below 75° C. and discharging. The method has a complicated process and unstable product performance, which is not suitable for popularization.

Chinese patent application CN 201610370195.8 disclosed a method for preparing castor oil polyester polyol and application thereof in controlled-release fertilizer, which comprises steps of: using castor oil as a raw material and small molecular alcohol as a modifier; preparing high hydroxyl value castor oil polyol through transesterification reaction under with a catalyst, and then using a polybasic acid or anhydride as a modifier to catalyze a condensation reaction, so as to obtain castor oil polyester polyol with a hydroxyl value of 200-350 mgKOH/g; using castor oil polyester polyol as a white material and isocyanate as a black material, and preparing an enveloped controlled-release fertilizer through an in-situ reaction. The method modifies castor oil to prepare polyester polyol, and further prepares the enveloped controlled-release fertilizer. However, the castor oil modification process is uncontrollable, and the price of the castor oil is relatively high, which increases the production cost.

SUMMARY OF THE PRESENT INVENTION

In order to solve the above-mentioned problems and final novel application of sebacic acid by-product fatty acid, the present invention provides a sebacic acid by-product fatty acid polyester polyol for polyurethane controlled-release fertilizer envelope, as well as a preparation method and an application thereof. The polyester polyol prepared by the present invention is cross-linked with MDI on a surface of a fertilizer, so as to form a polyurethane controlled-release fertilizer envelope material, thereby providing a polyurethane controlled-release fertilizer. The present invention uses the sebacic acid by-product fatty acid as a raw material to synthesize the polyester polyol because the sebacic acid by-product fatty acid is low in price and low in cost, the prepared fertilizer has excellent envelope and controlled-release performance, product structure performance is stable, cost performance is high, and degradation performance is sufficient after being applied to soil. The present invention comprehensively uses the sebacic acid by-product.

Accordingly, in order to accomplish the above objects, the present invention provides technical solutions as follows.

First, the present invention provides a sebacic acid by-product fatty acid polyester polyol for a polyurethane controlled-release fertilizer envelope, comprising a polyester polyol synthesized by an esterification reaction with a sebacic acid by-product fatty acid as a raw material; wherein the sebacic acid by-product fatty acid is refined from a by-product produced during preparing a sebacic acid from a castor oil; the sebacic acid by-product fatty acid comprises, in weight percentage: a palmitic acid 15-25%, a stearic acid 10-16%, an oleic acid 45-57%, and a linoleic acid 12-28%.

Preferably:

the polyester polyol comprises at least two of compounds expressed by formulas (1), (2) and (3):

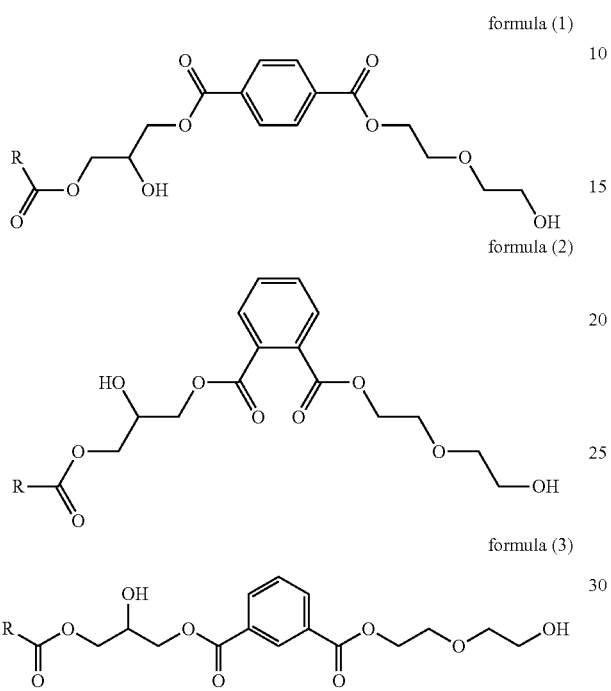

formula (1)

formula (2)

formula (3)

wherein R is selected from a group consisting of a palmitic acid group, a stearic acid group, an oleic acid group, and a linoleic acid group contained in the sebacic acid by-product fatty acid.

Palmitic acid is also known as hexadecanoic acid, whose chemical formula is $C_{16}H_{32}O_2$, is a saturated fatty acid.

Stearic acid, whose chemical formula is $C_{18}H_{36}O_2$, is a saturated fatty acid.

Oleic acid, whose chemical formula is $C_{18}H_{34}O_2$, is a monounsaturated fatty acid.

Linoleic acid, whose chemical formula is $C_{18}H_{32}O_2$, is an unsaturated fatty acid.

Preferably:

a hydroxyl value of the sebacic acid by-product fatty acid polyester polyol is 170-350 mgKOH/g.

The present invention also provides a method for preparing the sebacic acid by-product fatty acid polyester polyol, comprising steps of:

(1) distilling and refining the by-product produced during preparing the sebacic acid form the castor oil, so as to obtain the sebacic acid by-product fatty acid;

(2) putting the sebacic acid by-product fatty acid obtained in the step (1) and glycerin into a reactor, with a molar ratio of the sebacic acid by-product fatty acid:the glycerol as 1:(1-1.5); then heating to 160-240° C. for an esterification reaction, and keeping temperature for 1-6 hours; cooling when an acid value drops to below 10 mgKOH/g, so as to obtain a yellow transparent viscous liquid, which is sebacic acid by-product fatty acid glyceride, for subsequent use; and (3) adding a mixture of diethylene glycol and glycerol, a benzenedicarboxylic acid or an acid anhydride, and the sebacic acid by-product fatty acid glyceride obtained in the step (2) into a reaction vessel, wherein a weight percentage of each reactant is: the mixture of the diethylene glycol and the glycerin: 20-50%; the benzenedicarboxylic acid or the acid anhydride: 30-40%; and the sebacic acid by-product fatty acid glyceride: 20-50%;

then adding a catalyst and heating for a reflux reaction, keeping temperature at 220-260° C. and check the acid value; cooling to 180-220° C. when the acid value drops to below 5 mgKOH/g, and then performing vacuum distillation while controlling a vacuum degree at −0.065-0.095 MPa; cooling and discharging when the acid value of a rectification product drops to below 1.0 mgKOH/g and a mass fraction of a water content is less than 0.1%, so as to obtain the sebacic acid by-product fatty acid polyester polyol.

Preferably:

the step (1) comprises specific steps of: hydrolyzing the by-product produced during preparing the sebacic acid form the castor oil at a high temperature, distilling under a vacuum degree of −0.095-0.098 MPa, collecting distilled parts at 120-245° C., so as to obtain the sebacic acid by-product fatty acid.

Preferably, the high temperature for hydrolyzing is 120-180° C.

Preferably, the sebacic acid by-product fatty acid comprises, in weight percentage: the palmitic acid 15-25%, the stearic acid 10-16%, the oleic acid 45-57%, and the linoleic acid 12-28%.

Preferably, the acid value of the sebacic acid by-product fatty acid is 200-220 mgKOH/g, and an iodine value is 60-80.

Preferably:

in the step (3), the benzenedicarboxylic acid or the acid anhydride is a mixture of at least two of a terephthalic acid

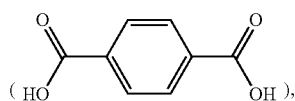

a phthalic acid

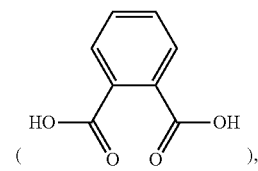 [SMILES: O=C(O)c1ccccc1C(=O)O]

a phthalic anhydride

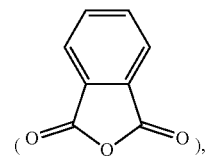

and an isophthalic acid

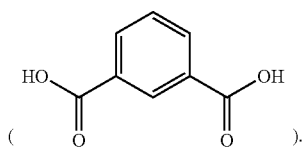 [SMILES: O=C(O)c1cccc(C(=O)O)c1]

When the reactant uses terephthalic acid as a main molecular structure, one of molecular structural formulas of the synthesized sebacic acid by-product fatty acid polyester polyol is:

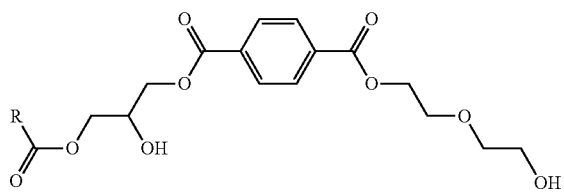

When the reactant uses phthalic acid or phthalic anhydride as the main molecular structure, one of the molecular structural formulas of the synthesized sebacic acid by-product fatty acid polyester polyol is:

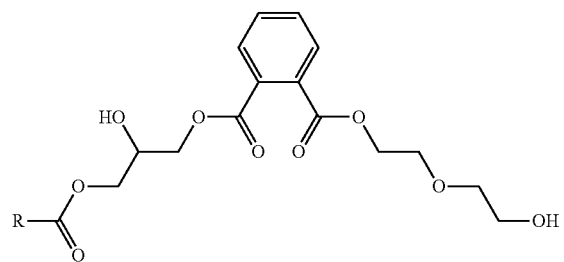

When the reactant uses isophthalic acid as the main molecular structure, one of the molecular structural formulas of the synthesized sebacic acid by-product fatty acid polyester polyol is:

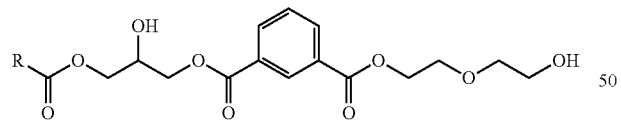

wherein R is selected from a group consisting of a palmitic acid group, a stearic acid group, an oleic acid group, and a linoleic acid group contained in the sebacic acid by-product fatty acid. It is understandable that R can also be selected from other fatty acid groups contained in the sebacic acid by-product fatty acid.

The preparation method provided by the present invention is relatively complicated, and main reactions principles are illustrated as follows:

step 1: distilling and refining the by-product produced during preparing the sebacic acid from the castor oil, so as to obtain the sebacic acid by-product fatty acid; wherein the sebacic acid by-product fatty acid is rich in palmitic acid, stearic acid, oleic acid, oleic acid, etc.;

step 2: according to the following reaction formula, preparing the sebacic acid by-product fatty acid glyceride (mainly fatty acid monoglycerides) through the esterification reaction between the sebacic acid by-product fatty acid and glycerin:

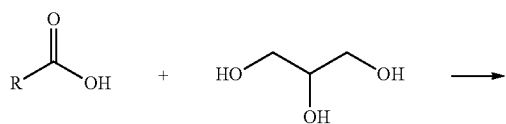

step 3: according to the following reaction formula, preparing the sebacic acid by-product fatty acid polyester polyol through esterification reaction between the sebacic acid by-product fatty acid glyceride obtained in the step 2 and with two carboxyl groups on the benzenedicarboxylic acid or the acid anhydride, as well as esterification reaction between diethylene glycol together with glycerol and the two carboxyl groups on the benzenedicarboxylic acid or the acid anhydride; wherein glycerin in the reaction can further improve product functionality; taking the main molecular structure of the terephthalic acid as an example, a possible reaction formula is as follows:

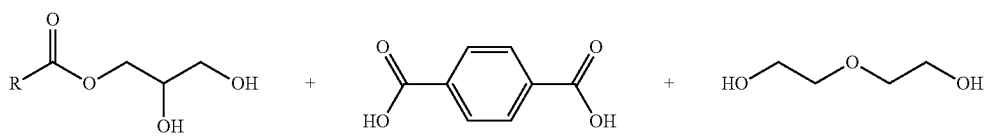

-continued

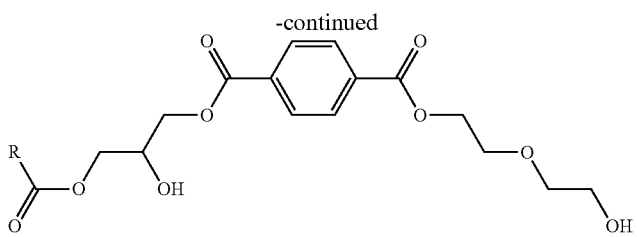

Based on the above reaction principles, a molecular system of the sebacic acid by-product fatty acid polyester polyol prepared by the method provided of the present invention comprises a variety of compounds with the benzenedicarboxylic acid as a main molecular structure, and the compounds expressed by the above formulas (1) (2) and (3) are possible structures. It can be understood that other compounds with other structures may also involved, as long as such compounds are produced under rational reaction principles and adopt the benzenedicarboxylic acid as the main molecular structure.

Preferably, in the step (3), the catalyst is an esterification catalyst. Preferably, the esterification catalyst is any one of an organic titanate catalyst, an organic tin catalyst, calcium oxide, and zinc acetate. Preferably, the organic titanate catalyst is either isopropyl titanate or butyl titanate.

Preferably, an addition amount of the esterification catalyst is 0.1-0.5% of a total reactant mass.

The present invention also provides applications of the above sebacic acid by-product fatty acid polyester polyol or the polyester polyol prepared by the above method in the polyurethane controlled-release fertilizer envelope or the polyurethane controlled-release fertilizer.

The present invention also provides a polyurethane controlled-release fertilizer envelope, which is prepared by cross-linking the sebacic acid by-product fatty acid polyester polyol or the polyester polyol prepared by the above method with isocyanate. The isocyanate is selected from a group consisting of polymethylene polyphenyl polyisocyanate, toluene diisocyanate, hexamethylene diisocyanate, diphenylmethane diisocyanate (MDI), liquefied MDI, isophorone diisocyanate, 1,6-hexylene diisocyanate (HDI), HDI trimer, trimethylhexamethylene diisocyanate, xylylene diisocyanate, and dimethyl biphenyl diisocyanate. MDI is preferred due to great price advantage and lower cost.

The present invention also provides a polyurethane controlled-release fertilizer, consisting of fertilizer particles and a polyurethane controlled-release fertilizer envelope on surfaces of the fertilizer particles. The polyurethane controlled-release fertilizer envelope is formed on the surfaces of the fertilizer particles by cross-linking the sebacic acid by-product fatty acid polyester polyol with isocyanate. The fertilizer particles may be common water-soluble elemental fertilizers such as: urea, ammonium sulfate, ammonium chloride, ammonium nitrate, monoammonium phosphate, diammonium phosphate, potassium chloride, potassium sulfate, potassium nitrate, magnesium sulfate, magnesium nitrate, zinc sulfate, copper sulfate and zinc chloride.

The present invention has at least the following beneficial effects:
1. According to the present invention, the method for preparing the polyester polyol for the polyurethane controlled-release fertilizer envelope adopts the sebacic acid fatty acid by-product as the main raw material. The sebacic acid by-product fatty acid is the by-product obtained during preparing the sebacic acid from the castor oil. Because the sebacic acid by-product fatty acid has limited application and is even discarded, it has caused great waste and environmental pollution. The present invention can not only provide new use of the fatty acid, but also relieve the production pressure of the sebacic acid. The present invention reuses the by-product, so as to comprehensively utilize the by-products obtained during preparing the sebacic acid from the castor oil.
2. The main raw material in the method of the present invention, the sebacic acid by-product fatty acid, is cheap and has a wide range of sources. The price is 4000-5000 RMB/ton, which is far lower than 11000-15000 RMB/ton of the castor oil, and is also lower than common vegetable oils (soybean oil, palm oil, linseed oil, etc.). The price of the polyester polyol produced is 6000-7000 RMB/ton, which means a very low production cost. When it comes to the enveloped polyurethane controlled-release fertilizer made of the polyester polyol synthesized by using the above sebacic acid by-product fatty acid, it is excellent in product performance and economical, which has extreme cost performance and price advantage, thereby improving the competitiveness of similar products in the market. After the enveloped polyurethane controlled-release fertilizer is applied to the soil, it shows a perfect combination of sufficient degradation, high performance, low cost and environmental protection. At the same time, the sebacic acid by-product is comprehensively and effectively used.
3. The present invention further uses the polyester polyol synthesized by the above method to prepare the enveloped polyurethane controlled-release fertilizer. The polyurethane controlled-release fertilizer envelope on the surfaces is a new type of bio-based degradable envelope material. Performance test results show that: the biodegradation rate of the polyurethane controlled-release fertilizer envelope material is up to 31.2%, an envelope rate is 2.0%-3.5%, and a release period is 60-150 days, which can meet the nutrients requirements for the growth of various crops, and can achieve sufficient controlled-release effect for the growth of plants. Furthermore, the envelope material is degradable, causing no pollution to the environment and no harm to the soil, which has a wide range of applications.
4. The polyurethane controlled-release fertilizer envelope material prepared by the present invention has stable quality, providing advantages of stable composition, stable structure and stable performance.

DETAILED DESCRIPTION OF THE PREFERRED EMBODIMENT

Referring to accompanying embodiments, the present invention will be further illustrated. However, the following embodiments are provided for clearly describe the present invention, and not intended to be limiting.

Embodiment 1

First, the present invention provides a method from preparing a sebacic acid by-product fatty acid, comprising steps of: hydrolyzing a by-product (purchased from companies that use the castor oil to produce the sebacic acid) produced during preparing a sebacic acid form a castor oil at 120-180° C., distilling under a vacuum degree of −0.095-0.098 MPa, collecting distilled parts at 120-245° C., so as to obtain the sebacic acid by-product fatty acid.

According to test results, the sebacic acid by-product fatty acid comprises, in weight percentage: the palmitic acid 15-25%, the stearic acid 10-16%, the oleic acid 45-57%, and the linoleic acid 12-28%.

According to the test results, an acid value of the sebacic acid by-product fatty acid is 200-220 mgKOH/g, and an iodine value is 60-80.

Embodiment 2

I. The embodiment 2 provides a method for preparing the sebacic acid by-product fatty acid polyester polyol, comprising steps of:
1) putting 1 mol sebacic acid by-product fatty acid obtained and 1 mol glycerin into a reactor; then heating to 160° C. for an esterification reaction, and keeping at 160° C. for 3 hours; cooling when an acid value drops to below 1.50 mgKOH/g, so as to obtain a yellow transparent viscous liquid, which is sebacic acid by-product fatty acid glyceride, for subsequent use; and
2) adding 330 g diethylene glycol, 10 g glycerol, 100 g phthalic anhydride, 300 g terephthalic acid, and 260 g sebacic acid by-product fatty acid glyceride obtained in the step 1) into a reaction vessel, then adding an isopropyl titanate catalyst with an addition amount of 0.1-0.5% of a total reactant mass, and heating for a reflux reaction; keeping temperature at 220° C. and checking the acid value; cooling to 180° C. when the acid value drops to below 1.50 mgKOH/g, and then performing vacuum distillation while controlling a vacuum degree at −0.065-0.095 MPa; cooling and discharging when the acid value of a rectification product drops to below 1.0 mgKOH/g and a mass fraction of a water content is less than 0.08%, so as to obtain the sebacic acid by-product fatty acid polyester polyol.

II. According to a Chinese national standard GB/T12008.3-2009, a phthalic anhydride method is used for measurement. The polyester polyol prepared in the embodiment 2 has a hydroxyl value of 180.5 mgKOH/g and a viscosity of 15100 CPS/25° C.

Embodiment 3

I. The embodiment 3 provides a method for preparing a enveloped polyurethane controlled-release fertilizer with the polyester polyol synthesized in the embodiment 2, comprising steps of:
weighing and adding 1 kg granular urea with a particle size of 2.00 mm-4.75 mm into a sugar coating machine for heating at 60° C.; mixing and adding 2.8 g polymeric MDI and 4.2 g polyester polyol prepared in the embodiment 1 into the granular urea, wherein an envelope material cross-links on surfaces of the granular urea to form a polyurethane controlled-release envelope, and a viscosity is increased; the envelope material becomes dense after being gradually cured on the surface of the urea for 3-5 minutes; so as to form the tough polyurethane controlled-release envelope with an envelope rate of 0.7%; repeating the above steps for 3 times, and adding 2.8 g polymeric MDI and 4.2 g polyester polyol for the second and third times, respectively, until the envelope rate is 2.1%; finally, adding paraffin of 0.2% of the total weight of the fertilizer to prevent adhesion between the fertilizer particles; cooling to 20° C. to obtain the enveloped polyurethane urea made of the sebacic acid by-product fatty acid polyester polyol.

II. Test on controlled-release performance of the enveloped controlled-release fertilizer prepared in the embodiment 3

A nutrient release period of the enveloped controlled-release fertilizer was tested at 25° C. by a static water extraction method, which was expressed as the number of days required for a cumulative nutrient release rate to reach 80%.

The nutrient release period of the enveloped controlled-release fertilizer prepared in the embodiment 3 is 60 days.

In order to illustrate biodegradability, the envelope material in the embodiment 2 was accurately weighed and buried in 58° C.±2° C. soil. After 6 months, samples were collected and dried in vacuum for 24 hours after surface soil was cleaned. After weighing, a sample weight loss rate is 31.2%.

Embodiment 4

I. The embodiment 4 provides a method for preparing the sebacic acid by-product fatty acid polyester polyol, comprising steps of:
1) putting 1 mol sebacic acid by-product fatty acid obtained and 1 mol glycerin into a reactor; then heating to 180° C. for an esterification reaction, and keeping at 180° C. for 3 hours; cooling when an acid value drops to below 1.50 mgKOH/g, so as to obtain a yellow transparent viscous liquid, which is sebacic acid by-product fatty acid glyceride, for subsequent use; and
2) adding 350 g diethylene glycol, 10 g glycerol, 200 g isophthalic acid, 200 g terephthalic acid, and 300 g sebacic acid by-product fatty acid glyceride obtained in the step 1) into a reaction vessel, then adding an organic tin catalyst with an addition amount of 0.1-0.5% of a total reactant mass, and heating for a reflux reaction; keeping temperature at 230° C. and checking the acid value; cooling to 190° C. when the acid value drops to below 1.63 mgKOH/g, and then performing vacuum distillation while controlling a vacuum degree at −0.065-0.095 MPa; cooling and discharging when the acid value of a rectification product drops to below 1.0 mgKOH/g and a mass fraction of a water content is less than 0.06%, so as to obtain the sebacic acid by-product fatty acid polyester polyol.

II. According to a Chinese national standard GB/T12008.3-2009, a phthalic anhydride method is used for measurement. The polyester polyol prepared in the embodiment 4 has a hydroxyl value of 207.3 mgKOH/g and a viscosity of 12300 CPS/25° C.

Embodiment 5

I. The embodiment 5 provides a method for preparing a enveloped polyurethane controlled-release fertilizer with the polyester polyol synthesized in the embodiment 4, comprising steps of:

weighing and adding 1 kg granular urea with a particle size of 2.00 mm-4.75 mm into a sugar coating machine for heating at 62° C.; mixing and adding 2.8 g polymeric MDI and 4.2 g polyester polyol prepared in the embodiment 4 into the granular urea, wherein an envelope material cross-links on surfaces of the granular urea to form a polyurethane controlled-release envelope, and a viscosity is increased; the envelope material becomes dense after being gradually cured on the surface of the urea for 3-5 minutes; so as to form the tough polyurethane controlled-release envelope with an envelope rate of 0.7%; repeating the above steps for 3 times, and adding 2.8 g polymeric MDI and 4.2 g polyester polyol for the second and third times, respectively, until the envelope rate is 2.1%; finally, adding paraffin of 0.2% of the total weight of the fertilizer to prevent adhesion between the fertilizer particles; cooling to 20° C. to obtain the enveloped polyurethane urea made of the sebacic acid by-product fatty acid polyester polyol.

II. Test on controlled-release performance of the enveloped controlled-release fertilizer prepared in the embodiment 5

A test method is the same as that of the embodiment 3.

A nutrient release period of the envelope controlled-release fertilizer prepared in the embodiment 5 is 60 days.

Embodiment 6

I. The embodiment 6 provides a method for preparing the sebacic acid by-product fatty acid polyester polyol, comprising steps of:
1) putting 1 mol sebacic acid by-product fatty acid obtained and 1.2 mol glycerin into a reactor; then heating to 200° C. for an esterification reaction, and keeping at 200° C. for 4 hours; cooling when an acid value drops to below 1.17 mgKOH/g, so as to obtain a yellow transparent viscous liquid, which is sebacic acid by-product fatty acid glyceride, for subsequent use; and
2) adding 260 g diethylene glycol, 20 g glycerol, 250 g phthalic acid, 50 g isophthalic acid, and 430 g sebacic acid by-product fatty acid glyceride obtained in the step 1) into a reaction vessel, then adding a butyl titanate catalyst with an addition amount of 0.1-0.5% of a total reactant mass, and heating for a reflux reaction; keeping temperature at 240° C. and checking the acid value; cooling to 200° C. when the acid value drops to below 1.17 mgKOH/g, and then performing vacuum distillation while controlling a vacuum degree at −0.065-0.095 MPa; cooling and discharging when the acid value of a rectification product drops to below 1.0 mgKOH/g and a mass fraction of a water content is less than 0.07%, so as to obtain the sebacic acid by-product fatty acid polyester polyol.

II. According to a Chinese national standard GB/T12008.3-2009, a phthalic anhydride method is used for measurement. The polyester polyol prepared in the embodiment 6 has a hydroxyl value of 266.9 mgKOH/g and a viscosity of 2860 CPS/25° C.

Embodiment 7

I. The embodiment 7 provides a method for preparing a enveloped polyurethane controlled-release fertilizer with the polyester polyol synthesized in the embodiment 6, comprising steps of:

weighing and adding 1 kg granular urea with a particle size of 2.00 mm-4.75 mm into a sugar coating machine for heating at 62° C.; mixing and adding 3.6 g polymeric MDI and 5.4 g polyester polyol prepared in the embodiment 6 into the granular urea, wherein an envelope material cross-links on surfaces of the granular urea to form a polyurethane controlled-release envelope, and a viscosity is increased; the envelope material becomes dense after being gradually cured on the surface of the urea for 3-5 minutes; so as to form the tough polyurethane controlled-release envelope with an envelope rate of 0.9%; adding 3.2 g polymeric MDI and 4.8 g polyester polyol for the second and third times with an envelope rate of 0.8%, respectively, until a final envelope rate is 2.5%; finally, adding paraffin of 0.2% of the total weight of the fertilizer to prevent adhesion between the fertilizer particles; cooling to 20° C. to obtain the enveloped polyurethane urea made of the sebacic acid by-product fatty acid polyester polyol.

II. Test on controlled-release performance of the enveloped controlled-release fertilizer prepared in the embodiment 7

A test method is the same as that of the embodiment 3.

A nutrient release period of the envelope controlled-release fertilizer prepared in the embodiment 7 is 90 days.

Embodiment 8

I. The embodiment 8 provides a method for preparing the sebacic acid by-product fatty acid polyester polyol, comprising steps of:
1) putting 1 mol sebacic acid by-product fatty acid obtained and 1.2 mol glycerin into a reactor; then heating to 220° C. for an esterification reaction, and keeping at 220° C. for 4 hours; cooling when an acid value drops to below 0.98 mgKOH/g, so as to obtain a yellow transparent viscous liquid, which is sebacic acid by-product fatty acid glyceride, for subsequent use; and
2) adding 300 g diethylene glycol, 50 g glycerol, 200 g phthalic acid, 100 g terephthalic acid, and 430 g sebacic acid by-product fatty acid glyceride obtained in the step 1) into a reaction vessel, then adding a calcium oxide catalyst with an addition amount of 0.1-0.5% of a total reactant mass, and heating for a reflux reaction; keeping temperature at 250° C. and checking the acid value; cooling to 210° C. when the acid value drops to below 0.98 mgKOH/g, and then performing vacuum distillation while controlling a vacuum degree at −0.065-0.095 MPa; cooling and discharging when the acid value of a rectification product drops to below 1.0 mgKOH/g and a mass fraction of a water content is less than 0.06%, so as to obtain the sebacic acid by-product fatty acid polyester polyol.

II. According to a Chinese national standard GB/T12008.3-2009, a phthalic anhydride method is used for measurement. The polyester polyol prepared in the embodiment 8 has a hydroxyl value of 347.6 mgKOH/g and a viscosity of 1760 CPS/25° C.

Embodiment 9

I. The embodiment 9 provides a method for preparing a enveloped polyurethane controlled-release fertilizer with the polyester polyol synthesized in the embodiment 8, comprising steps of:
weighing and adding 1 kg granular urea with a particle size of 2.00 mm-4.75 mm into a sugar coating machine for heating at 65° C.; mixing and adding 3.2 g polymeric MDI and 4.8 g polyester polyol prepared in the embodiment 8 into the granular urea, wherein an envelope material cross-links on surfaces of the granular urea to form a polyurethane controlled-release envelope, and a viscosity is increased; the envelope material becomes dense after being gradually cured on the surface of the urea for 3-5 minutes; so as to form the tough polyurethane controlled-release envelope with an envelope rate of 0.8%; adding 3.2 g polymeric MDI and 4.8 g polyester polyol for the second time with an envelope rate of 0.8%, and adding 3.6 g polymeric MDI and 5.4 g polyester polyol for the third time with an envelope rate of 0.9%, until a final envelope rate is 2.5%; finally, adding paraffin of 0.2% of the total weight of the fertilizer to prevent adhesion between the fertilizer particles; cooling to 20° C. to obtain the enveloped polyurethane urea made of the sebacic acid by-product fatty acid polyester polyol.

II. Test on controlled-release performance of the enveloped controlled-release fertilizer prepared in the embodiment 9

A test method is the same as that of the embodiment 3.

A nutrient release period of the envelope controlled-release fertilizer prepared in the embodiment 9 is 90 days.

Embodiment 10

I. The embodiment 10 provides a method for preparing the sebacic acid by-product fatty acid polyester polyol, comprising steps of:
1) putting 1 mol sebacic acid by-product fatty acid obtained and 1.5 mol glycerin into a reactor; then heating to 240° C. for an esterification reaction, and keeping at 240° C. for 5 hours; cooling when an acid value drops to below 1.24 mgKOH/g, so as to obtain a yellow transparent viscous liquid, which is sebacic acid by-product fatty acid glyceride, for subsequent use; and
2) adding 200 g diethylene glycol, 20 g glycerol, 200 g phthalic acid, 100 g terephthalic acid, and 500 g sebacic acid by-product fatty acid glyceride obtained in the step 1) into a reaction vessel, then adding a zinc acetate catalyst with an addition amount of 0.1-0.5% of a total reactant mass, and heating for a reflux reaction; keeping temperature at 260° C. and checking the acid value; cooling to 220° C. when the acid value drops to below 1.24 mgKOH/g, and then performing vacuum distillation while controlling a vacuum degree at −0.065-0.095 MPa; cooling and discharging when the acid value of a rectification product drops to below 1.0 mgKOH/g and a mass fraction of a water content is less than 0.05%, so as to obtain the sebacic acid by-product fatty acid polyester polyol.

II. According to a Chinese national standard GB/T12008.3-2009, a phthalic anhydride method is used for measurement. The polyester polyol prepared in the embodiment 10 has a hydroxyl value of 277.5 mgKOH/g and a viscosity of 3530 CPS/25° C.

Embodiment 11

I. The embodiment 11 provides a method for preparing a enveloped polyurethane controlled-release fertilizer with the polyester polyol synthesized in the embodiment 10, comprising steps of:
weighing and adding 1 kg granular urea with a particle size of 2.00 mm-4.75 mm into a sugar coating machine for heating at 65° C.; mixing and adding 2.8 g polymeric MDI and 4.2 g polyester polyol prepared in the embodiment 10 into the granular urea, wherein an envelope material cross-links on surfaces of the granular urea to form a polyurethane controlled-release envelope, and a viscosity is increased; the envelope material becomes dense after being gradually cured on the surface of the urea for 3-5 minutes; so as to form the tough polyurethane controlled-release envelope with an envelope rate of 1.0%; repeating for three times and adding 4 g polymeric MDI and 6 g polyester polyol for the second and third times, respectively, until a final envelope rate is 3.0%; finally, adding paraffin of 0.2% of the total weight of the fertilizer to prevent adhesion between the fertilizer particles; cooling to 20° C. to obtain the enveloped polyurethane urea made of the sebacic acid by-product fatty acid polyester polyol.

II. Test on controlled-release performance of the enveloped controlled-release fertilizer prepared in the embodiment 11

A test method is the same as that of the embodiment 3.

A nutrient release period of the envelope controlled-release fertilizer prepared in the embodiment 11 is 120 days.

Embodiment 12

I. The embodiment 12 provides a method for preparing the sebacic acid by-product fatty acid polyester polyol, comprising steps of:
1) putting 1 mol sebacic acid by-product fatty acid obtained and 1.5 mol glycerin into a reactor; then heating to 200° C. for an esterification reaction, and keeping at 200° C. for 5 hours; cooling when an acid value drops to below 1.04 mgKOH/g, so as to obtain a yellow transparent viscous liquid, which is sebacic acid by-product fatty acid glyceride, for subsequent use; and
2) adding 200 g diethylene glycol, 30 g glycerol, 300 g phthalic acid, 56 g isophthalic acid, and 350 g sebacic acid by-product fatty acid glyceride obtained in the step 1) into a reaction vessel, then adding an organic tin catalyst with an addition amount of 0.1-0.5% of a total reactant mass, and heating for a reflux reaction; keeping temperature at 240° C. and checking the acid value; cooling to 200° C. when the acid value drops to below 1.04 mgKOH/g, and then performing vacuum distillation while controlling a vacuum degree at −0.065-0.095 MPa; cooling and discharging when the acid value of a rectification product drops to below 1.0 mgKOH/g and a mass fraction of a water content is less than 0.07%, so as to obtain the sebacic acid by-product fatty acid polyester polyol.

II. According to a Chinese national standard GB/T12008.3-2009, a phthalic anhydride method is used for measurement. The polyester polyol prepared in the embodiment 12 has a hydroxyl value of 181.4 mgKOH/g and a viscosity of 23500 CPS/25° C.

Embodiment 13

I. The embodiment 13 provides a method for preparing a enveloped polyurethane controlled-release fertilizer with the polyester polyol synthesized in the embodiment 12, comprising steps of:
weighing and adding 1 kg granular urea with a particle size of 2.00 mm-4.75 mm into a sugar coating machine for heating at 68° C.; mixing and adding 4.4 g polymeric MDI and 6.6 g polyester polyol prepared in the embodiment 12 into the granular urea, wherein an envelope material cross-links on surfaces of the granular urea to form a polyurethane controlled-release envelope, and a viscosity is increased; the envelope material becomes dense after being gradually cured on the surface of the urea for 3-5 minutes; so as to form the tough polyurethane controlled-release envelope with an envelope rate of 1.1%; adding 4.8 g polymeric MDI and 7.2 g polyester polyol for the second and third times, respectively, until a final envelope rate is 3.5%; finally, adding paraffin of 0.2% of the total weight of the fertilizer to prevent adhesion between the fertilizer particles; cooling to 20° C. to obtain the enveloped polyurethane urea made of the sebacic acid by-product fatty acid polyester polyol.

II. Test on controlled-release performance of the enveloped controlled-release fertilizer prepared in the embodiment 13

A test method is the same as that of the embodiment 3.

A nutrient release period of the envelope controlled-release fertilizer prepared in the embodiment 13 is 150 days.

Application Example

1. Sample: the enveloped polyurethane controlled-release fertilizer prepared in the embodiments 3, 5, 7, 9, 11 and 13.
2. The nutrient release period of the enveloped polyurethane controlled-release fertilizer prepared in the embodiments 3, 5, 7, 9, 11 and 13 were tested by the static water extraction at 25° C. Cumulative release rates of nitrogen in static water were detected by sampling in different days. The sampling was carried out at 24 h, 7 d, 28 d, 56 d, 60 d, 90 d, 120 d, 150 d, and finally the cumulative release rate of nitrogen in static water extraction of the enveloped urea of the above embodiments were recorded and shown in Table 1.

TABLE 1

Measurement data of cumulative release rate of nitrogen in static water extraction of enveloped urea of different embodiments

| Group | 24 h initial release rate of nitrogen | 7 d cumulative release rate of nitrogen | 28 d cumulative release rate of nitrogen | 56 d cumulative release rate of nitrogen | 60 d cumulative release rate of nitrogen | 90 d cumulative release rate of nitrogen | 120 d cumulative release rate of nitrogen | 150 d cumulative release rate of nitrogen |
|---|---|---|---|---|---|---|---|---|
| Embodiment 3 | 0.19 | 4.13 | 54.61 | 77.90 | 79.09 | | | |
| Embodiment 5 | 0.22 | 4.22 | 51.12 | 73.45 | 77.62 | | | |
| Embodiment 7 | 0.15 | 2.34 | 12.07 | 39.16 | 46.01 | 78.43 | | |
| Embodiment 9 | 0.18 | 3.37 | 10.19 | 41.48 | 49.15 | 82.87 | | |
| Embodiment 11 | 0.03 | 2.41 | 5.26 | 23.91 | 33.69 | 61.25 | 80.96 | |
| Embodiment 13 | 0.01 | 1.25 | 4.35 | 15.23 | 21.45 | 40.76 | 62.15 | 81.63 |

The foregoing descriptions are only the embodiments of the present invention and are not intended to be limiting. Although the present invention has been described in detail with reference to the foregoing embodiments, for those skilled in the art, the recorded technical solutions can be modified, or some of the technical features can be equivalently replaced. Such modification, equivalent replacement and improvement made within the spirit and principle of the present invention should be included in the protection scope of the present invention.

What is claimed is:

1. A sebacic acid by-product fatty acid polyester polyol for a polyurethane controlled-release fertilizer envelope, comprising a polyester polyol synthesized by an esterification catalyzed reaction with a sebacic acid by-product fatty acid as a raw material; wherein the sebacic acid by-product fatty acid is refined from a by-product produced during preparing a sebacic acid from a castor oil; the sebacic acid by-product fatty acid comprises, in weight percentage: a palmitic acid 15-25%, a stearic acid 10-16%, an oleic acid 45-57%, and a linoleic acid 12-28%, wherein:

the polyester polyol comprises at least two of compounds expressed by formulas (1), (2) and (3):

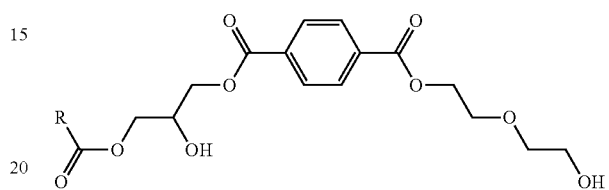

formula (1)

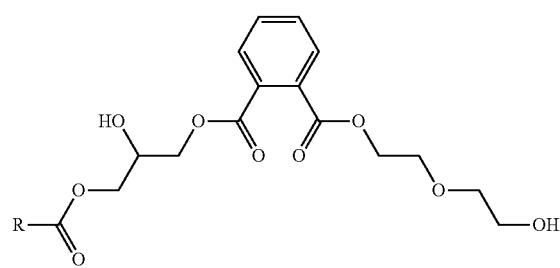

formula (2)

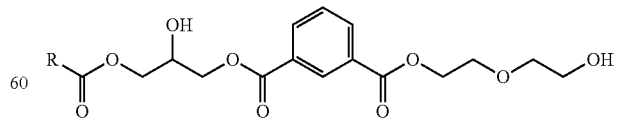

formula (3)

wherein R is selected from a group consisting of a palmitic acid group, a stearic acid group, an oleic acid group, and a linoleic acid group contained in the sebacic acid by-product fatty acid.

2. The sebacic acid by-product fatty acid polyester polyol, as recited in claim 1, wherein:
   a hydroxyl value of the sebacic acid by-product fatty acid polyester polyol is 170-350 mgKOH/g.

* * * * *